United States Patent [19]

Goldenberg

[11] Patent Number: 4,624,846

[45] Date of Patent: Nov. 25, 1986

[54] METHOD FOR ENHANCING TARGET SPECIFICITY OF ANTIBODY LOCALIZATION AND CLEARANCE OF NON-TARGET DIAGNOSTIC AND THERAPEUTIC PRINCIPLES

[75] Inventor: Milton D. Goldenberg, Short Hills, N.J.

[73] Assignee: Immunomedics, Inc., Newark, N.J.

[21] Appl. No.: 633,999

[22] Filed: Jul. 24, 1984

Related U.S. Application Data

[63] Continuation of Ser. No. 518,713, Jul. 29, 1983, abandoned.

[51] Int. Cl.⁴ .............. A61K 43/00; A61K 49/00; A61K 39/00; A61K 49/02; A61N 5/10
[52] U.S. Cl. .................. 424/1.1; 128/1.1; 128/659; 424/9; 530/387; 530/388
[58] Field of Search .............. 424/1.1, 9; 128/1.1, 128/659; 260/112 R; 530/387, 388

[56] References Cited

U.S. PATENT DOCUMENTS

| | | | |
|---|---|---|---|
| 4,311,688 | 1/1982 | Burchiel et al. | 424/1.1 |
| 4,323,546 | 4/1982 | Crockford et al. | 424/1.1 |
| 4,331,647 | 5/1982 | Goldenberg | 424/1.1 |
| 4,334,017 | 6/1982 | Plotkin et al. | 435/7 |
| 4,348,376 | 9/1982 | Goldenberg | 424/1.1 |
| 4,361,544 | 11/1982 | Goldenberg | 424/1.1 |
| 4,444,744 | 4/1984 | Goldenberg | 424/1.1 |
| 4,460,559 | 7/1984 | Goldenberg | 424/1.1 |
| 4,460,561 | 7/1984 | Goldenberg | 424/1.1 |

OTHER PUBLICATIONS

Bradwell et al., Lancet, Jan. 29, 1983, p. 247.
Begent et al., (I), Lancet, Oct. 2, 1982, pp. 739–742.
Begent et al., (II), Lancet, May 7, 1983, pp. 1047–1048.
Goodwin et al., Eur. J. Nucl. Med., 1984: 209–215.
Ryman et al., in Prog. Chem. Biol. Res., 162A: 299–308 (1982).

*Primary Examiner*—Christine M. Nucker
*Attorney, Agent, or Firm*—Millen & White

[57] ABSTRACT

A method for enhancing target specificity of antibody localization comprises injecting a second antibody specific to a labeled target-specific antibody to reduce the level of non-targeted circulating specific antibody, thereby increasing the localization ratio. The foregoing method is useful for imaging tumors and infectious lesions, and for therapy.

17 Claims, No Drawings

METHOD FOR ENHANCING TARGET SPECIFICITY OF ANTIBODY LOCALIZATION AND CLEARANCE OF NON-TARGET DIAGNOSTIC AND THERAPEUTIC PRINCIPLES

RELATED APPLICATIONS

This application is a continuation-in-part of U.S. Ser. No. 518,713, filed July 29, 1983, now abandoned.

BACKGROUND OF THE INVENTION

This invention relates to a method for reducing non-target levels of a diagnostic and/or therapeutic principle at a time subsequent to its injection in order to enhance the target specificity of the principle, e.g., for antibody localization for imaging and therapy.

Methods of tumor localization and therapy using labeled antibodies and antibody fragments specific to tumor-associated markers have been dislosed in Hansen et al, U.S. Pat. No. 3,927,193 and Goldenberg, U.S. Pat. Nos. 4,331,647, 4,348,376, 4,361,544, 4,460,559 and 4,460,561, and in the related applications of Goldenberg, U.S. Ser. Nos. 414,729 and 459,919, the disclosures of all of which are incorporated herein in their entirety by reference. In these patents and patent applications, subtraction techniques are disclosed for enhancing the resolution of tumor imaging by injecting a radiolabeled material capable of independent detection which can be used to subtract non-target background radiation in order to enhance the targeted specific antibody image. This can be achieved by using background agents which accumulate in the liver or spleen and can be used for subtraction of accumulated non-target label cleared by the reticuloendothelial system. An alternative subtraction technique makes use of indifferent immunoglobulin of the same or different species as that used to prepare the labeled specific antibody, the indifferent antibody being radiolabeled with a radionuclide capable of independent detection, so that the subtraction agent has substantially the same distribution kinetics as the specific antibody during the time period needed for imaging.

In both of the foregoing subtraction techniques, use of the subtraction agent involves introduction of additional radionuclides into the patient, independent detection of which facilitates a determination of the level of non-target radiation which can then be subtracted from the total radiation emmissions. This in turn permits more accurate detection of selective uptake of specific antibody by target tissues, thereby increasing the resolution of imaging methods. A disadvantage of these methods is that enhancement of resolution is achieved at the expense of introducing additional radioactive materials into the body, with all of the attendant side effects which may be produced thereby. It would be advantageous to be able to reduce the level of nontarget antibody without introduction of additional radioactivity.

It is known that specific antibodies can be entrapped in liposomes. Indeed, it was fond that humam IgM could be complexed after injection of liposomally-entrapped anti-IgM IgG in vivo, the complexes being removed by the reticuloendothelial system of the liver and/or spleen. It has also been proposed to extend this method to enhancing tumor images using radiolabeled primary markerspecific antibodies. Non-target antibody in the circulation and extravascular spaces would be cleared with liposomally-entrapped unlabeled second antibody directed against the first antibody, the clearance being effected by the reticuloendothelial system, thereby reducing the quantity of non-target radiolabeled antibody without the use of a second labeled material. It has been shown that digoxin in the circulation could be removed by administration of liposomally-entrapped anti-digoxin antibodies by means of clearance of the liposome/antigen-antibody complexes by the retriculoendothelial system. However, it was found that anti- digoxin antibody alone did not achieve this effect.

Antibodies to antigens which are produced by or associated with tumors have also been used for tumor therapy, as disclosed in the Goldenberg patents and patent applications cited hereinabove. These antibodies have been radiolabeled and/or combined with a boron-containing addend capable of activation with thermal neutrons. In these therapeutic techniques, it would be advantageous to be able to reduce the level of non-target antibody to enhance the specificity of localization of the therapeutic agent. It would also be desirable, although it has not been disclosed, to extend imaging and therapy beyond the use of antibodies to tumor-associated markers to encompass antibodies to antigens produced by or associated with infectious lesions of all sorts, and to the use of antibodies labeled with labels other than radionuclides.

OBJECTS OF THE INVENTION

One object of the present invention is to provide a method fo enhancing the target specificity of primary antibodies for diagnositc or therapeutic purposes.

Another object of the invention is to provide an improved method of tumor localization and/or therapy.

A further object of the invention is to provide methods for detecting and treating infectious lesions.

Upon further study of the specification and appended claims, further objects and advantages of this invention will become apparent to those skilled in the art.

SUMMARY OF THE INVENTION

These and other objects of the invention are achieved by providing, in a method for determining the location of a tumor which produces or is associated with a cytoplasmic, intracellular or cell-surface marker substance, which comprises injecting a human subject parenterally with a marker-specific antibody or antibody fragment radiolabeled with a pharmacologically inert radioisotope capable of detection using a photoscanning device, and subsequently scanning with said device to detect and locate the site or sites of uptake of said labeled antibody or antibody fragment by said tumor, the improvement comprising injecting said subject parenterally, at a time after injection of the marker-specific antibody or fragment sufficient to permit maximum selective uptake thereof by said tumor, and prior to photoscanning, with a second, non-radiolabeled antibody or antibody fragment specific against said marker-specific antibody or fragment, in an amount sufficient to decrease the level of circulating radiolabeled marker-specific antibody or fragment by 10–85% within 2–72 hours.

The invention further relates to a method of detecting and localizing an infectious lesion which produces or is associated with a marker substance, which comprises the steps of (a) injecting a human subject parenterally with a marker-specific antibody or antibody fragment labeled with a pharmacologically inert label capable of direct or indirect detection by an external, non-invasive detector; (b) at a time after injection of said labeled marker-specific antibody or fragment sufficient to permit maximum selective uptake thereof by said lesion, injecting said subject parenterally with a second antibody or fragment specific against said marker-specific antibody or fragment, in an amount sufficient to decrease the level of circulating labeled marker-specific antibody or fragment by 10–85% within 2–72 hours; and (c) subsequently scanning with said detector to detect and locate the site or sites of uptake of said labeled antibody or fragment by said lesion.

In a therapeutic aspect, the invention relates to a method of tumor or infectious lesion therapy, comprising injecting a human subject having a tumor or infectious lesion, parenterally, with a therapeutic amount of a primary antibody or antibody fragment specific against a marker produced by or associated with the tumor or lesion and labeled with a therapeutically effective radionuclide, boron addend, drug, toxin or a combination thereof; after a time sufficient to maximize selective uptake of the labeled primary antibody or antibody fragment by the tumor or lesion, injecting the subject parenterally with an unlabeled second antibody or antibody fragment specific against the primary antibody or antibody fragment, in an amount sufficient to decrease the level of circulating labeled primary antibody or antibody fragment by 10–85% within 2–72 hours; and, in the case of a boron-labeled primary antibody or antibody fragment, directing a beam of thermal neutrons at the site or sites of selective uptake of the labeled primary antibody or antibody fragment.

In general, enhanced clearance of a diagnostic or therapeutic principle, after optimal target localization, using second antibody according to the invention, will improve the localization ratio and/or therapeutic index of the targeted principle.

DETAILED DISCUSSION

The present inventor has discovered that the use of liposomes having a second antibody directed against primary antibody specific to an antigen produced by or associated with a tumor or lesion can be avoided, thereby providing a reproducible, simpler and potentially safer method of enhancing target specificity. The method of the invention can be applied to tumor imaging as well as the detection and localization of lesions associated with an antigen that is quantitatively increased over adjacent tissues. Also, the present method can be used to enhance the target specificity of therapeutic measures mediated by localized antibodies.

Antibodies and/or antibody fragments to tumor-associated marker substances are disclosed, inter alia, in the Goldenberg patents and patent applications incorporated herein by reference. Normally, such antibodies will include marker-specific immunoglobulin-G(IgG) and fragments containing the antigen-specific portions thereof, e.g., F(ab')$_2$, F(ab'), F(ab) and the like. Such antibodies and antibody fragments may be obtained by methods which are also disclosed in the referenced Goldenberg patents and patent applications. Unless otherwise noted, the term "antibody" in the remainder of this discussion will include whole IgG and IgG or IgM fragments, including hybrid fragments such as those disclosed in the referenced Goldenberg patents and patent applications.

It is particularly advantageous to use antibodies of high specificity, e.g., affinity-purified antibodies and/or monoclonal antibodies, in the present methods and compositions. Methods of obtaining such highly specific antibodies are also disclosed in the Goldenberg patents and patent applications incorporated herein by reference.

Antibodies to antigens produced by or associated with infectious lesions can be produced by the foregoing methods using the antigens, portions thereof or immunogenic compositions prepared therefrom. Such antigens include, but are not limited to, infectious organisms themselves, e.g., bacteria, fungi, parasites and viruses, but may also include marker substances which are produced by or accreted by or in the vicinity of infectious lesions.

Examples of antibodies to infectious organisms and/or antigens produced by or accreted by or in the vicinity of infectious lesions include, e.g., antibodies against variola virus, yellow fever virus, arboviruses, herpes viruses, myxoviruses, enteroviruses, rabies virus, hepatitis A and B viruses, *Chlamydia psittaci, Rickettsia prowazeki* and other rickettsia, *lymphocytic choriomeningitis virus, Neisseria meningitidis, Neisseria gonorrhoeae, Corynebacterium diphtheriae, Clostridium tetani, Bacillus anthracis, Yersinia pestis, Vibrio cholerae, salmonella* and *shigella* bacterial species, *staphylococci* species, *Reponema pallidum, leptospiral* species, *Mycobacterium leprae, Mycobacterium tuberculosis, Histoplasma capsulatum, Coccidioides immitis,* various streptococci, *Plasmodium falciparum* and other plasmodia, *Toxoplasma gondii, Leishmania donovani,* various trypanosomes, *Entameba histolytica, Giardia lambia, Trichinella spiralis, Strongyloides stercoralis, Antiostrongylus cantonensis, Wucheria bancrofti, Schistosoma mansoni* and other schistosomal helminths, *Paragonimus westermani,* echinococcal species, etc. Listings of disease-causing infectious organisms to which antibodies can be developed for use in this invention is contained in the second and subsequent editions of *Microbiology* by B. D. Davis et al, Harper & Row, Publishers, New York, 1973 and later, the disclosures of which are incorporated herein in their entirety by reference. Such infectious organisms may be those causing disease in humans or in animals, and the inventions herein are not restricted to any specific animal species, but may be applied for veterinary and human uses.

The foregoing primary antibodies are labeled with a radiolabel, i.e., a radionuclide capable of detection by a photoscanning device, e.g., a gamma scintillation camera. Suitable such radionuclides and methods of labeling antibodies therewith are disclosed in detail in the referenced Goldenberg patents and patent applications.

It is also possible to use other labels which can be detected by external methods. An example of such labels is the use of a paramagnetic species which, when localized by attachment to a marker-specific antibody, produces an effect in the immediate vicinity thereof which is detectable by a magnetic resonance detector, e.g., nuclear magnetic resonance. Such imaging techniques are described generally in NMR Imaging in Biomedicine, by P. Mansfield and P. G. Morris, *Advances in Magnetic Resonance (NMR) Imaging,* C. L. Partain et al, eds., W. B. Saunders Co., 1983.

Suitable paramagnetic labels include atoms or ions that slightly increase a magnetic field, having an odd number of electrons and a partially filled inner shell, such as is found in transition elements, rare earth elements, and those of the actinide series, and also occur in a few compounds with an even number of electrons and some metals. Such paramagnetic labels may include, e.g., manganese (II), copper (II), and cobalt (II). Other paramagnetic species may also be employed, e.g., manganese (III), copper (III), cobalt (III), chromium (II) and chromium (III), nickel (II) and nickel (III), and iron (II) and iron (III). Other suitable paramagnetic labels are contained in *NMR of Paramagnetic Molecules, Principles and Applications.* G. N. La Mar et al, eds., Academic Press, New York, 1973, the disclosure of which is incorporated herein in its entirety by reference.

In the case of metal ions, attachment of the label to the antibody may be effected by similar chelation techniques to those disclosed in the referenced Goldenberg patent applications for use with radionuclides. Additionally, methods for introducing paramagnetic labels into immunoglobulin molecules are disclosed in references describing the chelation of metal radionuclides to immunoglobulins, e.g., Paik et al, *J. Nucl. Med.* 23:37, 1982; Scheinberg et al, *Science* 215:1511, 1982; Hnatowich et al, *Science* 220:613, 1983.

Where the antibody is localized for therapeutic purposes, the label may be a radionuclide having therapeutic activity, i.e., emitting radiation which is toxic to tumor cells or infectious microorganisms, or a nuclide capable of being activated by thermal neutron absorption, especially boron-10, which absorbs thermal neutrons and is converted to an unstable boron isotope which decays by emission of alpha-particles. The primary antibody may also be conjugated with a suitable drug or toxin, or it may be effective without conjugation with a radionuclide or drug, the effectivness being enhanced by accelerated clearance of the primary antibody from the circulation and non-target spaces using the secondary antibody, according to the invention.

Where antibody is localized for diagnosis and/or therapy, the method of the invention increases the localization ratio of the specific primary antibody. The term "localization ratio" is used herein in its conventional sense, and means the ratio of target to non-target antibody. In general, the method of the invention will increase the localization ratio of a primary antibody by at least about 20%, preferably at least about 50%, and in some cases, considerably more.

The effectiveness of a primary antibody conjugated with a therapeutic principle, e.g., a radionuclide, boron addend, drug or toxin, will be assessed in terms of its therapeutic index. The term "therapeutic index" is used conventionally herein and means the ratio of therapeutic effects to undesirable side effects. It is often defined in terms of a quantitative measure of efficacy vs. toxicity in a standard model system, e.g., the ratio of the median lethal dose ($LD_{50}$) to the median effective dose ($ED_{50}$). The method of the invention results in an increase in the therapeutic index of primary antibody conjugated with a therapeutic principle, or used alone as a therapeutic agent, by clearing non-target primary antibody and/or detached therapeutic principle.

The second antibody can thus be specific to the primary antibody itself or to a drug, boron addend or toxin. It can also be specific to a carrier for a drug, toxin or radionuclide, especially a chelating agent for conjugating a radiometal, a paramagnetic metal, a therapeutic metal ion, e.g., Pt(II), or the like, to the primary antibody. Non-metallic conjugates, e.g., radioiodinated linking groups, or organic paramagnetic species such as nitroxides, can also be haptens to which the second antibody is specific.

Some conjugated diagnostic and/or therapeutic principles can detach from the primary antibody and fail to be targeted, or migrate from the target back into non-target spaces or into the circulatory system. The principle can be cleared with secondary antibody specific thereto, and this can be effected instead of or together with use of antibody-specific second antibody.

In another embodiment of the invention, primary antibody is labeled with both a diagnostic and a therapeutic principle. For example, a drug and a radioisotope or paramagnetic label will both be conjugated to primary antibody, or a labeled drug or toxin will be conjugated to primary antibody. This permits monitoring of localization, and clearance with second antibody in an amount and/or at a rate or frequency of administration that will optimize the increase in localization ratio and/or therapeutic index.

In yet another embodiment, a mixture of primary antibodies is used, carrying different diagnostic and/or therapeutic principles. Non-target primary antibody can be cleared with second antibody or a mixture of second antibodies specific to all primary antibodies, or selective clearance of particular non-target primary antibody and/or conjugated principle can be effected using second antibody to first one and then another primary antibody and/or principle, either continuously, periodically or sequentially.

The second antibody may be whole IgG or IgM, or a fragment of IgG or IgM, so long as it is capable of binding the primary antibody to form a complex which is cleared from the circulation and the non-target spaces more rapidly than the primary antibody itself. Clearance will generally be initiated by binding of the primary/secondary antibody complex to Fc receptors on macrophages. Preferably, the second antibody will be whole IgG or IgM. If the primary antibody is a fragment of IgG or IgM, it is preferable that the second antibody be whole IgG or IgM so that the primary/secondary complex retains the capability of activating the complement cascade. Conversely, where the primary antibody is whole IgG, the second antibody may be a fragment if the complex still retains complement-fixing capability. It is preferred that at least one of the primary/secondary pair be whole IgG or IgM.

The advantage of using IgM is that it forms a higher molecular weight complex with primary antibody or with detached conjugates, i.e., diagnostic and/or therapeutic principles such as drugs, toxins, boron addends, chelating agents, radionuclides, and the like. This will increase the rate and effectiveness of clearance of non-target primary antibody and/or principle, especially from blood. A disadvantage is that rapid clearance with IgM can cause an undesirably rapid accretion of cytotoxic agents in the reticuloendothelial system (RES).

Both IgM and certain isotypes of IgG, e.g., IgG3, have been found to be particularly effective in complement fixation, thereby offering advantages in clearance. Their use is generally preferred, where their specificity and avidity are also acceptably high. Mixtures of second antibody, including immunoglobulin classes, subtypes and/or species, can be used to further enhance clearance. In multimodal therapies, selective clearance can be effected by use of such mixtures for primary and for secondary andibody.

For example, a mixture of radiolabeled mouse anti-CEA-IgG and methotrexate-conjugated rat anti-CEA-IgG can be administered to a patient with colonic cancer. After localization is seen to be optimal, e.g., using subtraction with labeled indifferent IgG, according to the referenced Goldenberg patents, goat anti-mouse-IgG can be administered to clear non-target radioantibody, either preceded by, followed by or concomitant with anti-methotrexate-IgM to reduce the side effects of the drug. Other such embodiments will occur to the ordinary skilled clinician and will also fall within the scope of the invention.

The image-enhancing subtraction techniques disclosed in the above-referenced Goldenberg patents and applications are advantageously combined with the enhancement technique of the present invention to further improve imaging of tumors and infectious lesions. The accelerated clearance of labeled antibodies can increase the background radiation in the liver and spleen as well as the circulatory system where radionuclides are used as the primary antibody label. Injection of conventional subtraction agents, e.g., Tc-99m-labeled serum albumin, pertechnetate and/or sulfur colloid, is helpful to permit computerized subtraction of non-target background radiation from organs which effect clearance of antibodies from the circulatory system.

The Goldenberg patents and applications disclose an improved subtraction technique making use of normal-/indifferent IgG or fragments corresponding to the labeled specific antibody or fragment used for imaging. The indifferent antibody subtraction agent is labeled with a radionuclide capable of independent detection, and has the advantage that it has substantially the same kinetics of distribution and metabolism during a time sufficient for imaging as the specific antibody. The use of second antibody for enhanced clearance, according to the present invention, permits a further increase in resolution for this subtraction method, since it increases the ratio of target to non-target antibody distribution. It will be appreciated that the indifferent antibody and the specific antibody will preferably be from the same species or myeloma/hybridoma cell line so that the second antibody will clear the specific and the indifferent immunoglobulin from non-target areas at substantially the same rate. It will also be preferable, for this purpose to be accomplished, for the second antibody to be specific to a non-variable region of the specific and indifferent immunoglobulin species.

The secondary antibody may be derived from a different species from that of the primary antibody or from a host of a different strain of the same species as the primary antimarker antibody or antibody fragment, thus representing an allotypic antibody immunoreactive with the primary antibody of the same host species. These possibilities also apply to therapy. Moreover, the primary antibody may be of human derivation, obtained from patients having circulating immunoglobulins immunoreactive with the marker antigens of interest in this invention. Similarly, these human antibodies may be derived by hybridization methods used to generate hybridoma-monoclonal antibodies, whereby appropriate sensitized lymph cells of patients are isolated and used for fusion to appropriate human or other species' myeloma cells by known techniques of hybridoma production. Still another approach for generating human monoclonal antibodies against the target antigens of interest in this invention is by in vitro immunization methods, where human lymph cells are sensitized in culture with the appropriate antigen, these sensitized cells subsequently being fused with appropriate myeloma cells of human or other species origin. All these embodiments are possible with regard to diagnostic/detection imaging as well as for therapeutic applications.

The second antibody can be prepared by challenging an animal from a different species or inbred strain from that in which the primary antibody was raised with primary antibody and/or indifferent antibody from the same species as the primary antibody, using conventional procedures. In fact, a number of anti-species immunoglobulins and immunoglobulin fragments are available commercially. For example, if the primary antibody is a specific goat IgG, the second antibody can be rabbit anti-goat IgG, mouse, pig, donkey, horse or primate anti-goat IgG or the like. Alternatively, for example, use of sheep F(ab')2 as the labeled primary antibody can be combined with, e.g., rabbit anti-sheep IgG or F(ab')2. Monoclonal anti-species IgG is also available and is advantageously used as second antibody in the present process. Of course, the use of monoclonal antibodies as the specific primary antibody is also advantageous.

Similarly to procedures disclosed in the above-referenced Goldenberg patents and patent applications, it is advantageous to subject the second antibody to purification by affinity chromatography to minimize cross-reactivity with specific antibody or with blood group antigens and other potentially interfering substances. The affinity purification is preferably effected by passing the second antibody through one or more columns containing bound antibody of the species to which the second antibody must be immunoreactive. Recovery of the second antibody from the latter column is effected by conventional chaotropic agents, and final purification.

It will also be appreciated that the second antibody may be raised using primary antibody fragments and may be specific to the variable region of the primary antibody. This may be advantageous where the primary antibody is a small fragment, e.g., Fab or Fab', although it is also possible where the primary antibody is whole IgG, F(ab')2 or another larger fragment. In this case, however, the use of second antibody may be less effective in enhancing imaging in combination with the improved subtraction techniques of the Goldenberg references, since the second antibody will not be specific against the indifferent immunoglobulin.

Anti-idiotype antibodies to a primary antibody specific to a tumor associated antigen have been reported by, e.g., Nepom et al., *Proc. Natl. Acad. Sci. USA*, 81, 2864 (1984). Anti-idiotype antibodies to anti-hepatitis B antibodies have been reported by Kennedy et al., *Science*, 221, 853 (1983); and *J. Exp. Med.*, in press (1984). Use of such antiidiotypes as second antibody, in conjunction with the primary antibody to which they are uniquely specific, can achieve greatly enhanced localization ratios and serve as an alternative to subtraction to achieve high resolution in imaging and detection, as well as to increase therapeutic indices in therapy.

Use of a second antibody reactive with a species-specific primary antibody affords the use of a single second antibody in conjunction with mixtures of primary antibodies directed against different target markers or different epitopes of the same target antigen, as described in the Goldenberg references This would constitute a preferred embodiment of the current invention to allow increased accretion to the target of the primary antibody preparations using multiple target sites.

The second antibody is injected into the patient after sufficient time has elapsed following injection of the primary antibody to permit maximum selective uptake of primary antibody in the tumor or lesion to be imaged or treated therapeutically. In general, experience with the particular types of tumors or lesions and the particular types of primary antibodies employed for imaging or therapy will provide guidance to the clinician with regard to the optimal time for injection of second antibody. It is advantageous to use the improved subtraction technique of the Goldenberg references, using indifferent antibody as a subtraction agent, to monitor selective uptake so that a more precise determination can be made of the optimal time for second antibody injection.

Generally, injection of second antibody will be effected intravenously between about four and twenty-four hours after administration of the primary antibody. If primary antibody administration is not intravenous, but is effected by injection into body cavities or intrathecally, it may also be advantageous to inject at least a portion of the second antibody by the same injection technique, although it will also generally be advantageous to inject at least a portion of second antibody intravenously to accelerate clearance of primary antibody which has diffused into the circulatory system.

Applications of the present method for enhancing target specificity of antibody localization are advantageously made in the various therapeutic methods disclosed in the Goldenberg patents and patent applications, as well as in therapeutic measures designed to reduce or combat the effects of infectious lesions. Such applications in the area of cancer radiotherapy normally involve injection of a therapeutic amount of a radiolabeled antibody specific against a tumor-associated marker. After sufficient time for maximizing selective uptake of the labeled primary antibody by the cancerous tissues, an amount of the second antibody is injected sufficient to accelerate the clearance of circulating primary antibody. This has the advantage of removing cytotoxic antitumor agents from the circulatory system after selective uptake by the cancerous tissues to minimize undesirable side effects on healthy tissues and organs. The clinician will recognize that care must be taken to balance the advantage of accelerated clearance of cytotoxic agents with the possibility of excessive levels of cleared cytotoxic agents in the reticuloendothelial system. It may be desirable in certain cases to administer agents capable of blocking or deactivating the reticuloendothelial system in order to mediate excessive buildup of cytotoxic or radiopharmaceutical agents in the liver and/or spleen while at the same time preventing the accretion of cytotoxic or radiopharmaceutical agents in other organs or systems still less capable of tolerating them. Many methods have been tried to block the reticuloendothelial system, e.g. with substances, such as carbon, methyl palmitate, latex beads, dextran sulfate, and small unilamellar vesicles (liposomes), as described e.g. by Proffitt et al., *Science* 220: 502, 1983, and the references cited therein. Potentially toxic substances cannot be used clinically to block the RES, so that it may be preferable to use e.g. unlabeled liposomes or dextran sulfate as nontoxic, temporary blocking agents. In an improvement, Proffitt et al. (*Science* 220:502,1983) describe the use of vesicles containing aminomannose in the lipid bilayer for this purpose.

An especially attractive application of the present method is in conjunction with tumor therapy using boron-labeled antibodies activated by thermal neutron irradiation. Disclosure of such therapeutic methods is found in the referenced Goldenberg patents and patent applications and references noted therein. In these methods, antibodies to tumor-associated markers are functionalized with boron-containing addends and injected into patients for localization. After selective uptake has been optimized, thermal neutron irradiation is effected. Boron-10 atoms in the localized addends have a very high thermal neutron cross-section and absorb neutrons to form unstable radionuclides which emit alpha-particles whose maximun cytotoxic effect tends to be limited to the immediate tissues surrounding the site of localization of the vehicle carrying the boron addend. Thus, effective localization of born-labeled antibodies in tumor tissues provides a method of carrying a potentially cytotoxic agent to the tumor site, and activating it only after it is localized at the desired point of action.

Efficient clearing of non-target antibody would enhance the effectiveness of this treatment. One method of restricting the site of activation is to combine a radiolabel with a boron addend on a specific antibody to a tumor-associated marker and to use the radiolabel to detect the site or sites of localization, followed by irradiation with a well-collimated beam of thermal neutrons directed at the tumor sites. However, this may miss small tumors or tumors which are located in areas of high background antibody accumulation. On the other hand, total body neutron irradiation entails the risk of activating boron-containing species in non-cancerous tissue with resultant injury to healthy tissues which vitiates the effectiveness of the therapy. Use of second antibody, according to the invention, to facilitate rapid clearance of non-target antibody can increase the safety of more widespread thermal neutron irradiation while still maximizing the effect in target tissues. It may be possible to dispense with radiolabeling if a high ratio of target to non-target antibody can be achieved and clearance of the non-target antibody from the body can be effected before the level of targeted antibody is diminished to a point below a therapeutically effective quantity.

In therapeutic methods directed against infectious lesions, similar clinical strategies will be used. The primary antibody will be either an antibody which is specific against the infectious microorganism itself or an antibody specific against a substance produced by or associated with the infectious organism and/or the lesion produced thereby. The therapeutic primary antibdoy can also carry a therapeutically effective radionuclide, a boron addend, a drug or a combination thereof to the site of infection, where it is selectively localized. Again, clearance of non-targeted primary antibody through the use of second antibody, according to the invention, can enhance the target specificity of the therapeutic measure.

The procedure used will be similar to that employed for antitumor therapy. Even the methods of conjugating antitumor drugs to immunoglobulins, as described e.g. in the chapter by G. J. O'Neill, The Use of Antibodies as Drug Carriers, in *Drug Carriers in Biology and Medicine,* G. Gregoriadis, ed., Academic Press, London, 1979; in Arnon et al., *Recent Results in Cancer Res.* 75:236, 1980; in Moolton et al., *Immunolog. Rev.* 62:47, 1982, the disclosures of all of which are incorporated herein in their entirety by reference, are quite similar to the methods employed for coupling drugs effective against various disease-causing microorganisms, such as against bacteria, viruses, fungi and diverse parasites, to antibodies developed against these microorganisms, their products or antigens associated with their lesions. Such antimicrobial, antiviral, antiparasitic, and related drugs, such as e.g. sulfonamides, penicillins and cephalosporins, aminoglycosides tetracyclines and chloramphenicol, piperazine, chloroquine, diaminopyridines, metronidazole, isoniazid, rifampins, streptomycins, sulfones, rifampin, erythromycin, polymixins, nystatin, amphotericins, 5-fluorocytosine, 5-iodo-2'-deoxyuridine, 1-adamantanamine, adenine arabinoside, amanitins, are preferred for coupling to appropriate specific antibodies and antibody fragments. Various potential antimicrobial agents for use in this invention are listed in Goodman and Gilman's *The Pharmacological Basis of Therapeutics*, Sixth Edition, A. G. Gilman et al., eds., Macmillan Publishing Co., New York, 1980, the contents of which is incorporated herein in its entirety by reference. Various conditions appropriate and desirable for targeting drugs to specific target sites have been reviewed e.g. by Trouet et al., in *Targeting of Drugs*, G. Gregoriadis et al., eds., Plenum Press, New York and London, 1982, pp. 19-30, the contents of which is incorporated herein in its entirety, including the entire volume, by reference.

The amount of second antibody introduced will generally be that amount which can decrease the circulating primary antibody by 10-85% within 2-72 hours. The ratio of second antibody to primary antibody which will affect this clearance will depend upon the binding properties of the primary second antibody pair. Preliminary screening in vitro can be used to provide an initial estimate of the appropriate ratio. The screen will be used to determine the ratio of second antibody to primary antibody required to obtain a precipitin band in e.g. a gel diffusion test, this then indicating the general range of the molar ratio of second antibody to primary antibody, and which may serve as a measure of the lower limit for the ratio since in vivo application may require a higher ratio of second antibody to primary antibody than is indicated by such in vitro tests.

In practice, the molar ratio of second antibody to primary antibody will generally be in the range of about 5-50, although this range should not be considered limitative. Molar ratios of second antibody to primary antibody of 15-25, and preferably 20-25, have been found to be advantageous where both the primary and the second antibody are whole IgG.

The use of second antibody for clearance and enhanced target localization of primary antibody has revealed several surprising and unexpected characteristics of the localization process. It has been shown in certain cases that injection of second antibody can decrease the level of specific antibody taken up by a tumor, compared to the amount taken up by the tumor in the absence of second antibody. This suggests that accretion of specific antibody by tumor tissues is dependent to some extent on the amount of specific antibody in the circulation, so that rapid clearance of specific antibody reduces the total amount of such antibody that can recirculate through the tumor, thereby reducing the total amount which is bound by the target tissues. Moreover, antibody which is initially bound to the tumor tissues but is subsequently released is less likely to be replenished because of the diminished supply of specific antibody in the circulation. It is likely that this effect depends to a considerable extent on the time at which second antibody is injected with respect to the time of initial injection of primary antibody and that it can be minimized by appropriate timing of the second antibody injection.

On the other hand, injection of mixture of specific antibody and indifferent immunoglobulin showed that selective uptake, expressed as the localization ratio (ratio of specific antibody to indifferent antibody), is significantly higher in target tissues, e.g., tumors, than in non-target tissues, e.g., liver, spleen, kidneys and blood, for subjects which had been injected with second antibody, starting as early as about two hours postinjection of the second antibody and increasing with time. This enhancement of localization ratios is not due to a more rapid clearance of indifferent antibody from the circulation, since the indifferent antibody and the specific antibody levels in the circulation remained in substantially the same ratio to one another as in the initial injection, as least for a time after the second antibody injection which is sufficient for imaging. Moreover, localization ratios in non-target tissues other than the blood remain substantially constant throughout the period of observation.

These results suggest that the amount of indifferent immunoglobulin in the tumor is dependent primarily upon the level of indifferent immunolglobulin in the blood rather than upon specific antigen interaction. Thus, as the level of non-specific immunoglobulin in the circulation falls, its level in target tissues falls correspondingly, while the specific antibody remains more firmly bound in the target tissue by antigen/antibody binding. It will be appreciated that the subtraction techniques using indifferent immunoglobulin, disclosed in the referenced Goldenberg patents and patent applications, will be particularly enhanced using the second antibody technique according to the present invention. The higher localization ratios in target tissues will permit greater resolution, with the corollary that even smaller tumors and/or lesions may be detected.

Both the primary and second antibody preparations may be prepared and administered as disclosed in the referenced Goldenberg patents and patent applications for analogous purposes. As noted hereinabove, the method of injection of second antibody need not correspond entirely to the method of injection of the primary specific antibody, especially if primary antibody is not injected intravenously or intraarterially.

The use of antibodies, by themselves or coupled with radionuclides and/or drugs, for the more selective treatment of neoplasms and infectious lesions, may in all likelihood require divided and repeated doses, thus requiring intermitent application of the second antibody preparation for achieving improved target localization. Therefore, this will require various individualized treatment regimens for both the primary and secondary antibodies. Whereas repeated application of primary antibody would preferably require the use of antibody fragments to decrease host sensitization to the immunoglobulin species upon repeated application, the application of whole immunoglobulin as the second antibody might be more limiting in terms of repeated application. Hence, it would be advantageous to administer the second antibody at particularly high doses (e.g. above 100 mg immunoglobulin protein) in order to induce host tolerance to this protein. On the other hand, use of hybridization techniques (e.g. by in vitro sensitization of human lymph cells) to generate human monoclonal antibodies directed against various species immunoglobulins comprising the primary antibodies of interest in this invention would contribute toward alleviating this potential problem, and thus would be a preferred method for repeated application of secondary antibody in therapeutic regimens.

Recently, monoclonal antibodies have been used to diagnose infectious diseases by immunological methods (Nowinski et al., Science 219:637, 1983), but these approaches have not been applied to detecting the sites of disease of for selective antimicrobial therapy. It is important to appreciate that there is a great diversity in the different kinds of antigens recognized by immunizing animals or by generating monoclonal antibodies. In some instances the monoclonal antibodies recognize broad categories of antigens distributed on a variety of microorganisms, whereas in other cases these antibodies recognize only a small class of organisms. For purposes of initial diagnosis and detection of a lesion caused by an as yet unproven organism, it is preferable to select antibodies which recognize all or large numbers of a particular phylogenetic group but not those of other, unrelated groups. Once the phylogenetic groups is identified, then subsequent antibody detection measures can be employed to obtain further restriction and more specific diagnosis. In some instances, antibody mixtures are preferable, since different epitopes distributed among the different organisms on their products may require multiple antibody preparations. This may be particularly advantageous for subsequent therapy, either using antibodies alone or with antimicrobial drugs coupled thereto. Thus, in certain cases of infectious disease (or tumor types, for that matter), the development of antibody mixtures is required to compensate for the limited specificity of certain individual monoclonal antibodies.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in anyway whatsoever. In the following examples, all temperatures are set forth uncorrected in degrees Celsius; unless otherwise indicated, all parts and percentages are by weight.

Antibodies used in these examples are highly specific, either prepared by conventional immunization followed by complement inactivation, adsorption to remove hemagglutination components and affinity purification against crossreactive antigens and specific antigen, or they are hybridoma-derived monoclonal antibodies.

EXAMPLES

EXAMPLE 1

Tumor Localization

The localization procedure described in Example 6 of U.S. Pat. No. 4,348,376 is followed, except that the initial injection of I-131-labeled anti-CEA IgG is effected without incorporation of I-123-labeled indifferet IgG (i.e., the injectable preparation is prepared according to Example 5(a) instead of according to Example 5(b) of U.S. Pat. No. 4,348,376), and that 250 μg of labeled primary antibody are injected, the labeling being such that the total I-131 content is 2 mCi; 6 hours after injection of the goat anti-CEA IgG, a sterile solution of affinity purified swine anti-goat IgG (Boehringer Mannheim Biochemicals) containing human serum albumin and phosphate-buffered saline, in physiological saline, is injected by intravenous infusion; and that 18 and 28 hours post-injection of second antibody, the patient is imaged with a gamma-scintillation camera, without the use of either Tc-99m-labeled blood-pool or interstitial agents or indifferent IgG. Sufficient reduction of non-target radioactivity is achieved by the clearance technique of the present invention to permit identification of the area of selective uptake without the use of computer-assisted subtraction, revealing the focus of targeted, localized uptake of labeled specific antibody in the posterior pelvis, corresponding with the area of recurrence confirmed by transmission computed tomography, in this patient having a history of recurrent colonic carcinoma.

Similar successful imaging is achieved using primary antibodies specific to other cell-surface, cytoplasmic or intracellular markers, either in the form of whole antibodies or antibody fragments, with either whole IgG or fragments, preferably whole IgG as second antibody. This can be achieved, inter alia, by effecting similar modification in the examples of the other referenced Goldenberg patents and patent applications relating to tumor imaging.

EXAMPLE 2

Detection of Infectious Lesions

A solution is prepared of F(ab')$_2$ fragment of goat IgG specific against Herpes simplex virus type-1(HSV-1), the fragment being prepared according to the method of Example 1 of U.S. Pat. No. 4,331,647, except that in place of anti-CEA IgG, murine monoclonal anti-HSV-1 antibody is used (cf. Nowinski et al., Science 219:637, 1983 for description of murine monoclonal antibodies prepared against HSV-1).

The fragment is radiolabeled according to Example 1 of U.S. Pat. No. 4,331,647, using I-131, and a sterile solution of the purified F(ab')$_2$ anti-HSV-1 labeled antibody is prepared according to Example 5 of U.S. Pat. No. 4,331,647.

A patient suspected of having encephalitis caused by HSV-1 is injected intravenously with 0.5 mg I-131-anti-HSV-1 F(ab')$_2$, having a total radioactivity of 3 mCi. Three hours after infusion of the primary antibody fragment, 10 mg of rabbit anti-mouse Ig is administered intravenously. The patient is scanned with a gamma-scintillation camera 21 hours after second antibody injection, and an area of selective accretion of label is detected and imaged in the area of the left skull. Improved contrast can be achieved using I-123 or In-111 labels on the primary anti-HSV-1 antibody fragment, and using emission tomography (tomoscintigraphy).

Similar detection and imaging of infectious lesions can be effected by substituting whole antibodies or antibody fragments specific against other infectious organisms and/or antigens associated with lesions produced by or associated with such organisms. Included among these are imaging processes using other labels than radionuclides, e.g., paramagnetic substances which permit imaging using nuclear magnetic resonance detection techniques.

The skilled art worker will recognize that data taken from gamma-scintographic camera scans are stored in a computer and can be displayed using a variety of graphic representations, including the use of different colors to represent different intensities of radiation, correlated with the individual data points. In subtraction, the activity level of the labeled normal immunoglobulin is equalized with the activity level of the labeled specific antibody in at least one non-target area, a background level value for the labeled antibody is calculated for each data point, and the resultant background value is subtracted from the total antibody radioactivity value, pixel-bypixel, to generate a value for the activity of targeted antibody for each data point, which is then used to generate a related output signal.

EXAMPLE 3

Tumor Therapy

Using the procedures of U.S. Pat. No. 4,348,376, especially Examples 1, 5 and 7 thereof, a patient with a liver metastasis of colonic cancer is given a dose of 4 mg of affinity purified goat anti-CEA IgG, labeled with 60 mCi of I-131 radionuclide. Twenty-four and 48 hours after administration of the primary therapeutic antibody dose, injections of donkey anti-goat IgG (whole IgG) are administered intravenously at doses of 30 mg each. This regimen is repeated weekly for a period of three weeks. Conventional liver scans and transmission computed tomography of the liver reveal, three weeks after interruption of therapy, that the liver metastasis has decreased by about 40%. This three-week cycle of therapy is repeated, using primary antibody of a different species and second antibody of yet another species than goat or donkey, so as to avoid hypersensitivity reactions, after a period of time sufficient for the patient's bone marrow function to return to normal. Alternatively, the radioantibody therapy cycles may be interspersed with therapeutic cycles using drug-conjugated primary antibody, e.g., daunomycin-conjugated anti-CEA IgG, followed 24 and 48 hours later with a sufficient dose of antibody against the primary antibody to clear at least about 40% of the primary antibody from the circulation and extravascular spaces without significantly lowering its level of selective uptake in the tumor.

EXAMPLE 4

Tumor Neutron Therapy

Using the procedure of Example 8 of U.S. Pat. No. 4,361,544, a patient having germ-cell cancer of the testis, with secondary abdominal metastatis, is treated with I-131-B-10-labeled anti-HCG IgG, prepared analogously to the boron and radiolabeled anti-AFP IgG prepared according to Examples 5 and 6 of the referenced patent. Twenty-four hours after injection of the primary antibody, the patient is injected intravenously with an amount of donkey antigoat IgG sufficient to reduce the circulating level of primary antibody by at least about 75% within about 48 hours. Twenty-four hours post injection of second antibody, the patient is scanned with a gamma-scintillation camera, and the primary testicular tumor as well are larger abdominal metastases are imaged. A collimated thermal neutron beam is then directed at the sites of antibody localization, and a lower intensity thermal neutron beam is also swept over the abdominal cavity, again following the procedure of Example 8 of U.S. Pat. No. 4,361,544.

Use of higly boron-loaded antibody fragments specific to antigens produced by or associated with brain tumors or infectious lesions, followed by the enhanced clearance technique of the invention and thermal neutron irradiation of the skull after sufficient time to permit clearance of substantially all non-localized antibody, provides an especially effective therapeutic technique for treating such tumors and lesions which heretofore have not been readily treatable.

EXAMPLE 5

Anti-viral Tumor Therapy

A 54-year old male patient is know to have hepatocellular cancer which has not responded well to conventional chemotherapy. Since there is an association of this tumor type with hepatitis B virus, a murine monoclonal antibody against hepatitis B surface antigen (HBsAg), anti-HBs, as developed in several laboratories (Shih et al., *J. Virol. Meth.* 1:257, 1980; David et al., *Med. Lab. Sci.* 38:341, 1981; Wands and Zurawski, *Gastroenterol.* 80:225, 1981; is used for the detection and therapy of this liver carcinoma. A 3 mCi dose of I-131-anti-HBs (0.3 mg IgG protein) is administered to the patient i.v., followed 8 hours later with a 40 mg i.v. dose of rabbit anti-murine IgG. Using 99m-Tc-sulfur colloid as a liver subtraction agent (to remove increased accretion in the liver of the rabbit-murine immune complexes), the liver cancer is revealed by external gamma (planar) scintigraphy and by tomoscintigraphy. Having shown the selective uptake of murine anti-HBs in the liver carcinoma, the same preparation is given at 2-divided doses weekly of 10 mg primary antibody each, followed 48 hours later by a single application of 150 mg rabbit anti-mouse IgG. Prior to administration of the radioiodinated murine monoclonal (primary) antibody, the patient is given Lugol's solution and potassium perchlorate orally to reduce uptake of I-131 in the thyroid and gastrointestinal mucosae. The primary antibody administered for therapy is labeled with I-131 so that a dose of 80 mCi is given weekly. This regimen is repeated biweekly for three applications, and then repeated in this cycle again 3 months later. Two months after the second treatment cycle, conventional liver scans and computed tomography indicate a 50% reducrtion of the liver lesion, with an accompanying reduction of serum alpha-fetoprotein levels from an initial 1,200 ng/ml elevation to a value of 200 ng/ml. Four months later, a third antibody administration is undertaken, this consisting of a single dose of I-131-labeled goat antibody against alpha-fetoprotein (AFP), i.v., comprising 5 mg of goat IgG protein and 60 mCi of I-131. Six hours after this injection, 80 mg of donkey anti-goat IgG is slowly infused. This regimen is repeated 3 weeks later. After another 8 weeks, serum AFP is noted to have fallen to less than 80 ng/ml and the liver lesion seen on computed tomography appears to be slightly less than the previous examination following the second course of therapy.

Similar successful imaging and therapy is achieved using primary antibodies to infectious lesions caused by microorganisms, particularly bacteria, viruses, and multicellular parasites, either in the form of whole antibodies or antibody fragments and preferably with whole IgG as the second antibody. This can be achieved, inter alia, by effecting similar modification in the examples related above and of the other referenced Goldenberg patents and patent applications relating to tumor imaging and therapy.

The preceding examples can be repeated with similar success by substituting the generically or specifically described reactants and/or operating conditions of this invention for those used therein.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. In a method for determining the location of a tumor which produces or is associated with a cytoplasmic, intracellular or cell-surface marker substance, which comprises injecting a human subject parenterally with a marker-specific antibody or antibody fragment labeled with a pharmacologically inert radioisotope capable of detection using a photoscanning device, or with a paramagnetic conjugate capable of detection with a magnetic resonance detector, and subsequently scanning with said device or detector to detect and locate the site or sites of uptake of said labeled antibody or antibody fragment by said tumor, the improvement comprising injecting said subject parenterally, at a time after injection of the marker-specific antibody or fragment sufficient to permit maximum selective uptake thereof by said tumor, and prior to scanning, with a second, non-labeled antibody or antibody fragment specific against said marker-specific antibody or fragment, in an amount sufficient to decrease the level of circulating labeled marker-specific antibody or fragment by 10–85% within 2–72 hours.

2. A method of detecting and localizing an infectious lesion which produces or is associated with a marker substance, which comprises the steps of:

(a) injecting a human subject parenterally with a marker-specific antibody or antibody fragment labeled with a pharmacologically inert radioisotope capable of detection using a photoscanning device, or with a paramagnetic conjugate capable of detection with a magnetic resonance detector;

(b) at a time after injection of said markerspecific antibody or fragment sufficient to permit maximum selective uptake thereof by said lesion, injecting said subject parenterally with a second antibody or fragment specific against said markerspecific antibody or fragment, in an amount sufficient to decrease the level of circulating labeled marker-specific antibody or fragment by 10–85% within 2–72 hours; and (c) subsequently scanning with said device or detector to detect and locate the site or sites of uptake of said labeled antibody or fragment by said lesion.

3. A method of tumor or infectious lesion therapy, comprising injecting a human subject having a tumor or infectious lesion, parenterally, with a therapeutic amount of primary antibody or antibody fragment specific against a marker produced by or associated with said tumor or lesion and labeled with a therapeutically effective radionuclide, boron addend, drug, toxin or a combination thereof; after a time sufficient to maximize selective uptake of the labeled primary antibody or antibody fragment by said tumor or lesion, injecting the subject parenterally with a second antibody or antibody fragment specific against said primary antibody or antibody fragment, or against said addend, drug or toxin, a carrier therefor or a chelating agent for said radionuclide, in an amount sufficient to decrease the level of circulating labeled primary antibody or antibody fragment by 10–85% within 2–72 hours; and, in the case of a boron-labeled primary antibody or antibody fragment, directing a beam of thermal neutrons at the site or sites of selective uptake of said labeled antibody or antibody fragment.

4. In a method for determining the location of a tumor which produces or is associated with a cytoplasmic, intracellular or cell-surface marker substance, which comprises injecting a human subject parenterally with a marker-specific antibody or antibody fragment labeled with a pharmacologically inert radioisotope capable of detection using a photoscanning device, or with a paramagnetic conjugate capable of detection with a magnetic resonance detector, and subsequently scanning with said device or detector to detect and locate the site or sites of uptake of said labeled antibody or antibody fragment by said tumor, the improvement comprising injecting said subject parenterally, at a time after injection of the marker-specific antibody or fragment sufficient to permit maximum selective uptake thereof by said tumor, and prior to scanning, with a second, non-labeled antibody or antibody fragment specific against said marker-specific antibody or fragment, in an amount sufficient to increase the localization ratio by at least about 20% within 2–72 hours.

5. A method of detecting the localizing an infectious lesion which produces or is associated with a marker substance, which comprises the steps of:

(a) injecting a human subject parenterally with a marker-specific antibody or antibody fragment labeled with a pharmacologically inert radioisotope capable of detection using a photoscanning device, or with a paramagnetic conjugate capable of detection with a magnetic resonance detector;

(b) at a time after injection of said marker-specific antibody or fragment sufficient to permit maximum selective uptake thereof by said lesion, injecting said subject parenterally with a second antibody or fragment-specific against said marker-specific antibody or fragment, in an amount sufficient to increase the localization ratio by at least about 20% within 2–72 hours; and (c) subsequently scanning with said device or detector to detect and locate the site or sites of uptake of said labeled antibody or fragment by said lesion.

6. A method of tumor or infectious lesion therapy, comprising injecting a human subject having a tumor or infectious lesion, parenterally, with a therapeutic amount of a primary antibody or antibody fragment specific against a marker produced by or associated with said tumor or lesion and labeled with a therapeutically effective radionuclide, boron addend, drug, toxin or a combination thereof; after a time sufficient to maximize selective uptake of the labeled primary antibody or antibody fragment by said tumor or lesion, injecting the subject parenterally with a second antibody or antibody fragment specific against said primary antibody or antibody fragment, or against said addend, drug or toxin, a carrier therefor or a chelating agent for said radionuclide, in an amount sufficient to increase the therapeutic index by at least about 10%; and, in the case of a boron-labeled primary antibody or antibody fragment, directing a beam of thermal neutrons at the site or sites of selective uptake of said labeled antibody or antibody fragment.

7. The method of either of claims 2 or 5, wherein said label is a radiolabel, and wherein prior to photoscanning, a second substance is injected into the subject, said second substance being radiolabeled with a radioisotope emitting at a different energy from the marker-specific antibody or antibody fragment label and capable of independent detection by said photoscanning device, the level of activity of said second substance being used to determine the background activity due to nontargeted specific antibody or antibody fragment, said background activity being subtracted from the total activity of the specific antibody or antibody fragment, whereby the activity of substantially only the targeted antibody or antibody fragment is determined.

8. The method of claim 7, wherein said second substance is the corresponding indifferent immunoglobulin or fragment from the same species as said labeled marker-specific primary antibody or antibody fragment.

9. The method of any of claims 2, 3, 5 or 6, wherein at least one of said labeled primary antibody or antibody fragment and said second antibody or antibody fragment is whole IgG.

10. The method of any of claims 2, 3, 5 or 6, wherein said second antibody is whole IgG or IgM.

11. The method of any of claims 2, 3, 5 or 6, wherein the molar ratio of said second antibody or antibody fragment to said marker-specific primary antibody or antibody fragment is from about 5 to about 40.

12. The method of claim 3 or 6, wherein the second antibody is specific to said boron addend, drug, toxin, carrier or chelating agent.

13. The method of either of claims 1 or 4, wherein said label is a radiolabel, and wherein prior to photoscanning, a second substance is injected into the subject, said second substance being radiolabeled with a radioisotope emitting at a different energy from the marker-specific antibody or antibody fragment label and capable of independent detection by said photoscanning device, the level of activity of said second substance being use to determine the background activity due to non-targeted specific antibody or antibody fragment, said background activity being subtracted from the total activity of the specific antibody or antibody fragment, whereby the activity of substantially only the targeted antibody or antibody fragment is determined.

14. The method of claim 13, wherein said second substance is the corresponding indifferent immunoglobulin or fragment from the same or different species as said labeled marker-specific primary antibody or antibody fragment.

15. The method of either of claims 1 or 4, wherein at least one of said labeled primary antibody or antibody fragment and said second antibody or antibody fragment is whole IgG.

16. The method of either of claims 1 or 4, wherein said second antibody is whole IgG or IgM.

17. The method of either of claims 1 or 4, wherein the molar ratio of said second antibody or antibody fragment to said labeled marker-specific primary antibody or antibody fragment is from about 5 to about 40.

* * * * *